(12) United States Patent
Jung et al.

(10) Patent No.: US 12,332,227 B2
(45) Date of Patent: *Jun. 17, 2025

(54) MULTI-SENSOR GAS DETECTOR

(71) Applicant: Honeywell Analytics Inc., Charlotte, NC (US)

(72) Inventors: Changyoung Jung, Seoul (KR); Jinkwang Cho, Seoul (KR); Sang Hoon Hur, Seoul (KR); Jae Hwan Lee, InCheon (KR)

(73) Assignee: Honeywell Analytics Inc., Charlotte, NC (US)

( * ) Notice: Subject to any disclaimer, the term of this patent is extended or adjusted under 35 U.S.C. 154(b) by 54 days.

This patent is subject to a terminal disclaimer.

(21) Appl. No.: 18/217,040

(22) Filed: Jun. 30, 2023

(65) Prior Publication Data
US 2023/0358716 A1 Nov. 9, 2023

Related U.S. Application Data

(63) Continuation of application No. 16/673,591, filed on Nov. 4, 2019, now Pat. No. 11,913,926.

(51) Int. Cl.
*G01N 33/00* (2006.01)
*G01N 1/26* (2006.01)

(52) U.S. Cl.
CPC .......... *G01N 33/0031* (2013.01); *G01N 1/26* (2013.01)

(58) Field of Classification Search
CPC .. G01N 33/0031; G01N 1/26; G01N 33/0009; G01N 33/0021; G01N 27/26
See application file for complete search history.

(56) References Cited

U.S. PATENT DOCUMENTS

| | | |
|---|---|---|
| 7,329,389 B2 | 2/2008 | Horovitz et al. |
| 7,504,631 B2 | 3/2009 | May |
| | (Continued) | |

FOREIGN PATENT DOCUMENTS

| | | | |
|---|---|---|---|
| CN | 102023105 A | * | 4/2011 |
| CN | 104165740 A | * | 11/2014 |
| | (Continued) | | |

OTHER PUBLICATIONS

CN-102023105-A (Year: 2011).*
(Continued)

*Primary Examiner* — Kristina M Deherrera
*Assistant Examiner* — Fatemeh Esfandiari Nia
(74) *Attorney, Agent, or Firm* — Alston & Bird LLP

(57) ABSTRACT

Various example embodiments described herein relate to a sensor assembly. The sensor assembly includes a substrate and a disk for providing parallel gas flow to a plurality of sensing dies. The substrate defines a plurality of openings and an inlet conduit. The plurality of openings is adapted to receive at least one sensing die of the plurality of sensing dies. The inlet conduit is defined between a first end of the substrate and a second end of the substrate. The first end of the substrate is adapted to receive an inflow of a gas. The disk is adapted to be positioned below the substrate so that a top portion of the disk is exposed to the second end of the inlet conduit and the disk defines a passage for the gas to uniformly flow from the second end to a sensor head of the at least one sensing die.

19 Claims, 11 Drawing Sheets

(56) References Cited

U.S. PATENT DOCUMENTS

| | | | |
|---|---|---|---|
| 2012/0192643 A1 | 8/2012 | Speldrich et al. |
| 2016/0209382 A1 | 7/2016 | Shalom et al. |
| 2016/0299110 A1 | 10/2016 | Remondini |
| 2017/0370809 A1 | 12/2017 | Miller-Lionberg et al. |
| 2018/0356293 A1 | 12/2018 | Sebrand |
| 2019/0154551 A1 | 5/2019 | Richter et al. |

FOREIGN PATENT DOCUMENTS

| | | | | |
|---|---|---|---|---|
| CN | 206740735 U | * | 12/2017 | |
| CN | 206756789 U | | 12/2017 | |
| CN | 108469452 A | * | 8/2018 | |
| CN | 208350764 U | * | 1/2019 | |
| GB | 2536975 A | * | 10/2016 | ........... G01N 1/2273 |
| JP | 2019-045277 A | | 3/2019 | |

OTHER PUBLICATIONS

CN-104165740-A (Year: 2014).*
CN-108469452-A (Year: 2018).*
CN-206740735-U (Year: 2017).*
Advisory Action (PTOL-303) Mailed on Jun. 24, 2022 for U.S. Appl. No. 16/673,591.
CN Office Action Mailed on Jul. 11, 2023 for CN Application No. 202011146600, 12 page(s).
CN Office Action Mailed on Oct. 19, 2022 for CN Application No. 202011146600.0, 15 page(s).
English Translation of CN Office Action dated Jul. 11, 2023 for CN Application No. 202011146600, 6 page(s).
English Translation of KR Office Action dated Apr. 21, 2023 for KR Application No. 10-2022-0118098, 3 page(s).
English Translation of TW Office Action dated Feb. 14, 2023 for TW Application No. 109136858, 4 page(s).
English Translation of TW Office Action dated May 2, 2022 for TW Application No. 109136858, 4 page(s).
Final Office Action Mailed on Apr. 4, 2022 for U.S. Appl. No. 16/673,591.
KR Office Action Mailed on Apr. 21, 2023 for KR Application No. 10-2022-0118098, 3 page(s).
KR Office Action Mailed on Dec. 15, 2021 for KR Application No. 10-2020-0141942, 9 page(s).
Non-Final Office Action Mailed on Aug. 29, 2022 for U.S. Appl. No. 16/673,591.
Non-Final Office Action Mailed on Nov. 19, 2021 for U.S. Appl. No. 16/673,591.
Notice of Allowance and Fees Due (PTOL-85) Mailed on Apr. 3, 2023 for U.S. Appl. No. 16/673,591, 7 page(s).
Notice of Allowance and Fees Due (PTOL-85) Mailed on Jun. 30, 2023 for U.S. Appl. No. 16/673,591, 2 page(s).
TW Notice of Allowance Mailed on May 23, 2023 for TW Application No. 109136858, 4 page(s).
TW Office Action Mailed on Feb. 14, 2023 for TW Application No. 109136858, 5 page(s).
TW Office Action Mailed on Jan. 4, 2022 for TW Application No. 109136858, 11 page(s).
TW Office Action Mailed on Jun 2, 2021 for TW Application No. 109136858, 6 page(s).
TW Office Action Mailed on May 2, 2022 for TW Application No. 109136858, 7 page(s).
CN Notice of Allowance Mailed on Nov. 26, 2023 for CN Application No. 202011146600, 4 page(s).
English translation of CN Notice of Allowance dated Nov. 26, 2023 for CN Application No. 202011146600, 3 page(s).
English translation of KR Notice of Allowance dated Aug. 10, 2023 for KR Application No. 10-2022-0118098, 1 page(s).
KR Notice of Allowance Mailed on Aug. 10, 2023 for KR Application No. 10-2022-0118098, 7 page(s).
Notice of Allowance and Fees Due (PTOL-85) Mailed on Aug. 24, 2023 for U.S. Appl. No. 16/673,591, 2 page(s).

* cited by examiner

MULTI-SENSOR GAS DETECTOR

CROSS-REFERENCE TO RELATED APPLICATIONS

This application is a continuation of U.S. Non-Provisional patent application Ser. No. 16/673,591 (now U.S. Pat. No. 11,913,926B2), filed Nov. 4, 2019 and entitled "Multi-Sensor Gas Detector," the entire disclosure of which is hereby incorporated herein by reference in its entirety for all purposes.

TECHNOLOGICAL FIELD

The present disclosure relates generally to multi-sensor gas detectors, an assembly of multi-sensor gas detectors, and the system and apparatus associated therewith. More particularly, the invention pertains to detectors which provide parallel gas flow to a plurality of sensors.

BACKGROUND

In multi-sensor gas detector systems, gas flows either serially or in parallel. In serial gas flow, flow lines through which the gas flows are serially connected with each other. In such cases, a gas concentration passes through each sensor sequentially via the flow lines. In this regard, in some instances, sensor reading of at least one sensor (e.g., one that can be mounted in a rear part of the sensor assembly), corresponding to the detected gas, might be affected by non-uniform flow rate, pressure, and effect of other sensors on the gas concentration flowing through the other sensors. Accordingly, sensor assembly of existing multi-gas detector systems has associated challenges and limitations.

SUMMARY

Various example embodiments described herein relate to a sensor assembly including a substrate and a disk for providing parallel gas flow to a plurality of sensing dies. Further, the substrate defines a plurality of openings adapted to receive at least one sensing die of a plurality of sensing dies. In addition, the substrate defines an inlet conduit between a first end and a second end of the substrate. The first end of the substrate can be adapted to receive an inflow of a gas concentration. In accordance with one exemplary embodiment described herein, the disk includes a top portion and a bottom portion. Further, the disk can be adapted to be positioned below the substrate so that the top portion of the disk can be exposed to the second end of the inlet conduit and the disk defines a passage for the gas concentration to flow from the second end to a sensor head of the at least one sensing die.

Further, in another exemplary embodiment, the sensor assembly includes a housing having a top portion and a bottom portion. Further, in one exemplary embodiment, the top portion includes a substrate that defines a plurality of openings. In addition, the bottom portion of the housing includes a disk including a top portion and a bottom portion. In accordance with one exemplary embodiment described herein, the plurality of openings can be adapted to receive at least one sensing die of a plurality of sensing dies. In addition, the substrate further defines an inlet conduit between a first end of the substrate and a second end of the substrate. In this regard, the first end can be adapted to receive an inflow of a gas concentration. Further, the disk can be adapted to be positioned below the substrate so that the top portion of the disk can be exposed to the second end of the inlet conduit and so that the disk defines a passage for the gas concentration to flow from the second end to a sensor head of the at least one sensing die.

Further, in another exemplary embodiment, the sensor assembly is configured for providing parallel gas flow to a plurality of sensors. In accordance with one exemplary embodiment described herein, the sensor assembly includes a housing. Further, the housing includes a top cover, a bottom cover, and a substrate positioned between the top cover and the bottom cover. In this regard, the substrate defines a plurality of openings and an inlet conduit. Further, in another exemplary embodiment, the plurality of openings can be adapted to receive at least one sensor of a plurality of sensors. In addition, the inlet conduit can be defined between a first end of the substrate and a second end of the substrate. In accordance with one exemplary embodiment described herein, a disk includes a top portion and a bottom portion such that the top portion of the disk and a portion of the substrate define a passage for a gas concentration to flow from the second end of the substrate to a sensor head of the at least one sensor.

In accordance with one exemplary embodiment described herein, the top cover of the housing includes an inner portion and an outer portion. In addition, the bottom cover includes an inner portion and an outer portion. Further, in one exemplary embodiment, the inner portion of the top cover and the inner portion of the bottom cover can be adapted to cover and protect the substrate and internal components.

In accordance with one exemplary embodiment described herein, the bottom portion of the disk can be mounted on the inner portion of the bottom cover. Further, in one exemplary embodiment, the bottom portion of the disk defines a plurality of grooves.

In accordance with one exemplary embodiment described herein, the inner portion of the bottom cover can be adapted to include a plurality of locking elements. Further, in one exemplary embodiment, the plurality of locking elements can be adapted to be locked with the plurality of grooves.

In accordance with one exemplary embodiment described herein, the sensor assembly can include an outlet conduit mounted on the inner portion of the bottom cover. Further, in one exemplary embodiment, the outlet conduit can include a first opening at a central axis of the inner portion of the bottom cover and a second opening at an outer periphery of the outer portion of the bottom cover.

In accordance with one exemplary embodiment described herein, a second end of the inlet conduit can further include a plurality of flow lines extending from a second end of the outlet conduit to a first end of the outlet conduit, via the passage.

In accordance with one exemplary embodiment described herein, the first end can be configured to provide ingress of the gas concentration therethrough and the second end can be configured to provide an egress of the gas concentration via the passage.

In accordance with one exemplary embodiment described herein, the top portion of the disk can be adapted to define a plurality of bumps and a plurality of ribs. Further, in one exemplary embodiment, at least one bump of the plurality of bumps can be in proximity to the sensor head and define a channel between the at least one bump and the sensor head. In addition, at least one rib of the plurality of ribs can be adapted to be locked with the bottom cover of the housing.

In accordance with one exemplary embodiment described herein, the bottom portion of the disk can include an inner surface and an outer surface. Further, in one exemplary embodiment, the bottom surface of the disk can be mounted on the inner surface of the bottom cover.

The above summary is provided merely for the purpose of providing an overview of one or more exemplary embodiments described herein to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which are further explained within the following detailed description and its accompanying drawings.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1:
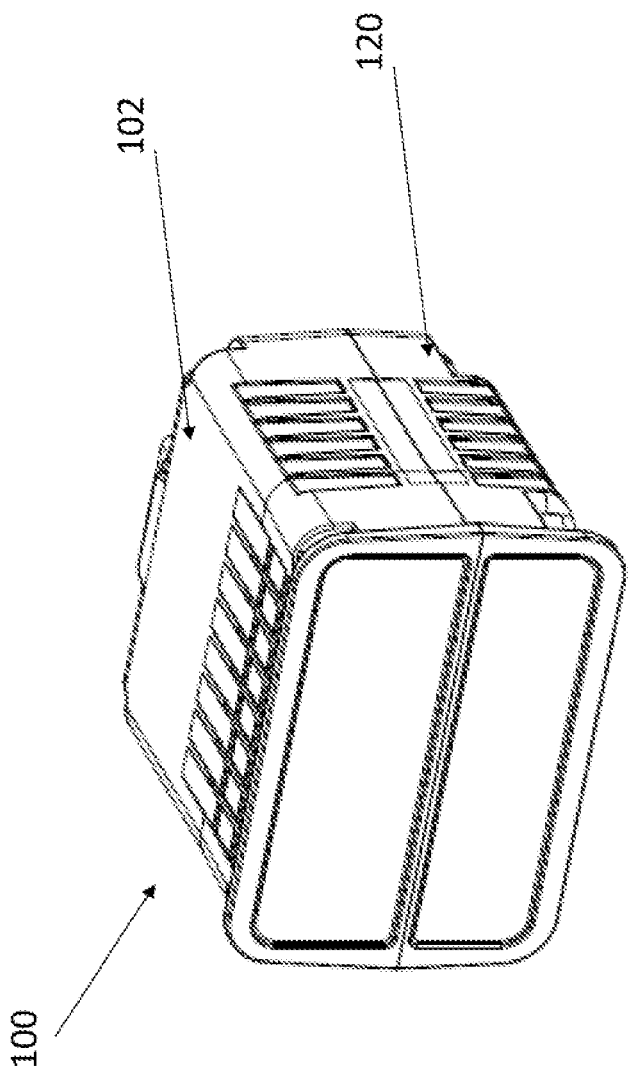
FIG. 1 depicts a perspective front view of a multi-sensor gas detector, in accordance with some example embodiments described herein.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout. Terminology used in this patent is not meant to be limiting insofar as devices described herein, or portions thereof, may be attached or utilized in other orientations.

The phrases "in one embodiment," "according to one embodiment," "in some embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The "housing" as described herein may correspond to an outer structure comprising a top cover and a bottom cover. Further, the housing according to the present invention can be designed as a module or an attachable sensor cartridge to cover and protect internal components of a sensor assembly. In addition, a shape and configuration of the housing including sensor cartridges can be selected based on the type of a target gas to be measured. Furthermore, the sensor cartridge can be detachable from the internal components.

The "printed circuit board" as described herein may comprise a circuitry which can be coupled to the multi-sensor gas detector. Further, in one exemplary embodiment, the printed circuit board (PCB) can be configured to determine a respective current for at least one sensor of the plurality of sensors. In this regard, the current corresponds to an amount of the target gas detected by the at least one sensor of the plurality of sensors.

According to some examples, the multi-sensor gas detector as described herein further includes a plurality of sensors for the detection of a plurality of gases. The plurality of sensors can be configured to detect various gas types such as, for example, oxygen, carbon monoxide, and hydrogen sulfide, but is not limited to these only.

In some example embodiments, the multi-sensor gas detector as described herein further includes a sensor gasket for sealing of a sensor. In one exemplary embodiment, the sensor gasket can include a gasket body which includes substantially planar sealing surfaces and a through passage. The sealing surfaces can be configured to align with a chamber or housing to be sealed.

The "substrate" as described herein may comprise an inner housing. For purposes of brevity, the inner housing can also be referred to hereinafter interchangeably as an inner cartridge throughout the description. Further, in one exemplary embodiment, the substrate can be made from a molded plastic housing having end walls defining a periphery of the substrate and a portion about a central axis of the substrate that defines a plurality of openings therebetween. Further, the substrate can be configured to receive at least one sensing die or at least one sensor in at least one opening of the plurality of openings in a first axial direction. Further, in one exemplary embodiment, the substrate can be formed from an insulting material.

The "disk" as described herein may comprise a flat planar disk substrate which has at least one engaging hole. The at least one engaging hole can be adapted to receive a flange from the bottom cover of the housing. Further, in one exemplary embodiment, the disk can be adapted to regulate a flow of the gas concentration in the housing. In some examples, the disk can be sandwiched between the substrate and a bottom cover of the housing of the sensor assembly. For the purposes of brevity, the disk can also be referred to hereinafter interchangeably as a cartridge disk plate throughout the description. Further, in one exemplary embodiment, the disk can be of any shape such as, but not limited to, a circular, rectangular, or cylindrical disk.

Typically, multi-sensor gas detectors can be used to detect a plurality of gases. Further, in the multi-sensor gas detectors, an oxidation or reduction reaction takes place at each sensor of a plurality of sensors and current is generated due to the oxidation or reduction reaction at one or more sensor of the plurality of sensors. Furthermore, in some examples, the multi-sensor gas detector can be used for the detection of either a plurality of target gases or only one target gas, in a gas concentration. The gas concentration, by this method, can lead to either oxidation or reduction reaction at a respective sensor of the plurality of the sensors. In this regard, the current generated based on the oxidation or reduction reaction is proportional to a concentration of a target gas. In this regard, it is possible to measure the concentration of the plurality of target gases through the value of current provided by the respective at least one sensor. To this end, generally, the at least one sensor of the plurality of the sensors is often exposed to the gas concentration. The plurality of sensors may be exposed to the gas concentration with variable pressure and velocity due to serial or parallel flow of the gas in the sensor assembly. In addition, the sequential flow or parallel flow of the gas takes more time to reach the at least one sensor with regards to the other sensors. Thus, the plurality of sensors is exposed to non-uniform conditions such as non-uniform exposure time, pressure, flow-rate, and velocity of the gas concentration. In addition, the multi-sensors are usually exposed to different pressure and flow rates which results in uneven time needed by each of the sensors to detect a target gas in a gas concentration.

In order to obviate the above-noted non-uniform conditions such as, for example, flow rate and exposure time, a parallel gas flow can be provided by using multiple inlets to the multi-sensor gas detector. Accordingly, parallel gas flow requires multiple outlets, resulting in a more complex multi-sensor gas detector. Further, in parallel flow sensors, multiple exhausts or outlets are needed at the same distance from each sensor to combine the distributed gas after sensing. The multiple exhausts require an additional structure for combining the distributed gas to vent off from the sensor assembly. In addition, the sensed value of the multi-sensor gas detector is distorted, delayed, and less accurate due to the different pressure received by each of the multi-sensors due to distorted flow rate and the effect of one sensor on the working of other sensors. Accordingly, there is an ongoing desire in the industry for multi-sensor gas detectors to be more robust, i.e., detectors that can avoid many pitfalls of existing multi-sensor gas detectors. Thus, it is desired to minimize non-uniformity of the parameters such as flow rate, pressure, structural complexities, and effect of gas from one sensor that affect the function of the other sensors. The structural complexities of the multi-sensor gas detector can be obviated by using a single inlet and a single outlet multi-sensor gas detector.

In this regard, the multi-sensor gas detector can be used with a housing and a disk structure which can be adapted to provide a uniform gas flow towards the plurality of sensors. The disk structure can be mounted in such a manner that the plurality of sensors receives a uniform and linear flow of the gas concentration.

Various exemplary embodiments described herein relate to a multi-sensor gas detector, and in particular to (i) detecting at least one target gas or a plurality of target gases from the gas concentration, (ii) obviating the effect of sensors on the neighboring sensors by providing independent flow lines to each of the plurality of sensors, (iii) increasing signal sensitivity due to a determination of a sensed current by each of the plurality of sensors respectively, and (iv) increasing signal to noise ratio due to linear and uniform exposure of the gas concentration to the plurality of sensors.

FIG. 1 depicts a perspective front view of a multi-sensor gas detector 100, in accordance with some example embodiments described herein. Further, in one exemplary embodiment, the multi-sensor gas detector 100 includes a housing top cover 102 and a housing bottom cover 120. In one exemplary embodiment, the housing top cover 102 and the housing bottom cover 120 can be adapted to shield a plurality of internal components from an outer environment. Further, in one exemplary embodiment, the housing bottom cover 120 can be coupled with the top cover 102 by any attachment means, for example, using screws, a snap fit arrangement, a nut and bolt assembly, or an adhesive.

Figure 2:
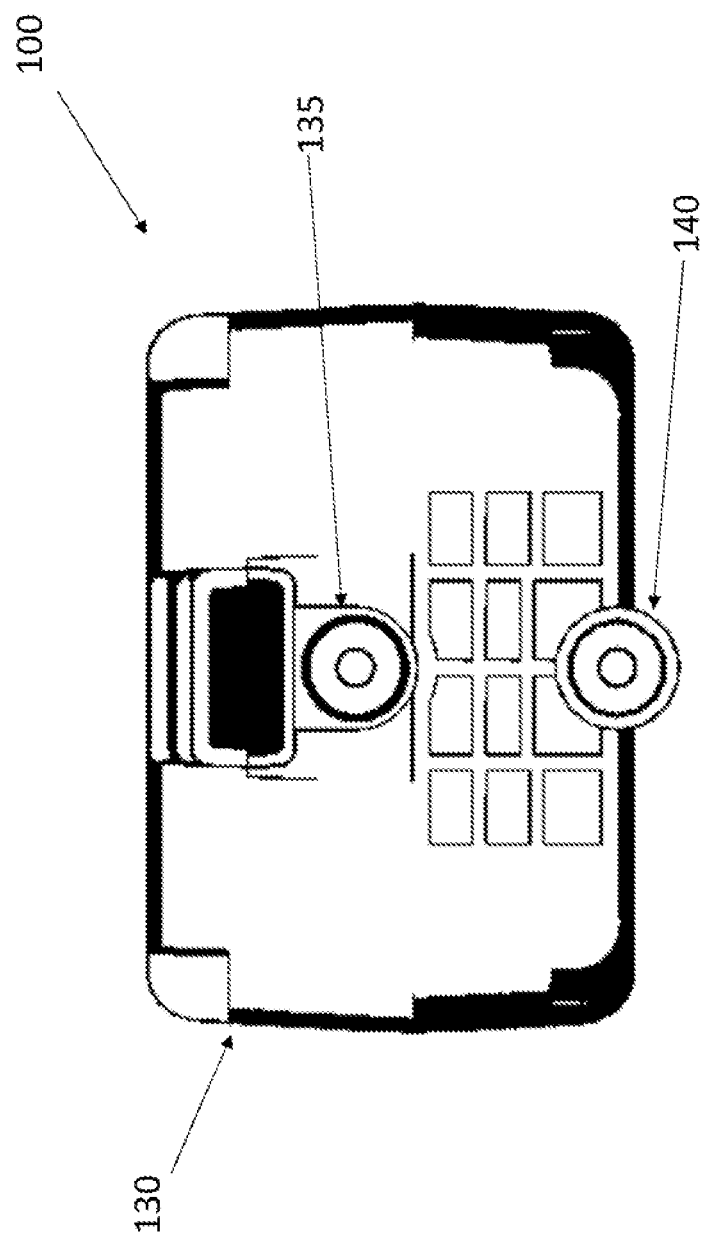
FIG. 2 depicts a perspective rear view of a multi-sensor gas detector, in accordance with some example embodiments described herein.

FIG. 2 depicts a perspective rear view 130 of a multi-sensor gas detector 100, in accordance with some example embodiments described herein. In one exemplary embodiment, the rear view 130 of the multi-sensor gas detector 100 includes a gas inlet hole 135 and a gas outlet hole 140. In one exemplary embodiment, the gas inlet hole 135 allows the ingress of a gas inside the multi-sensor gas detector 100 and the gas outlet hole 140 allows the gas to exit through it.

Figure 3:
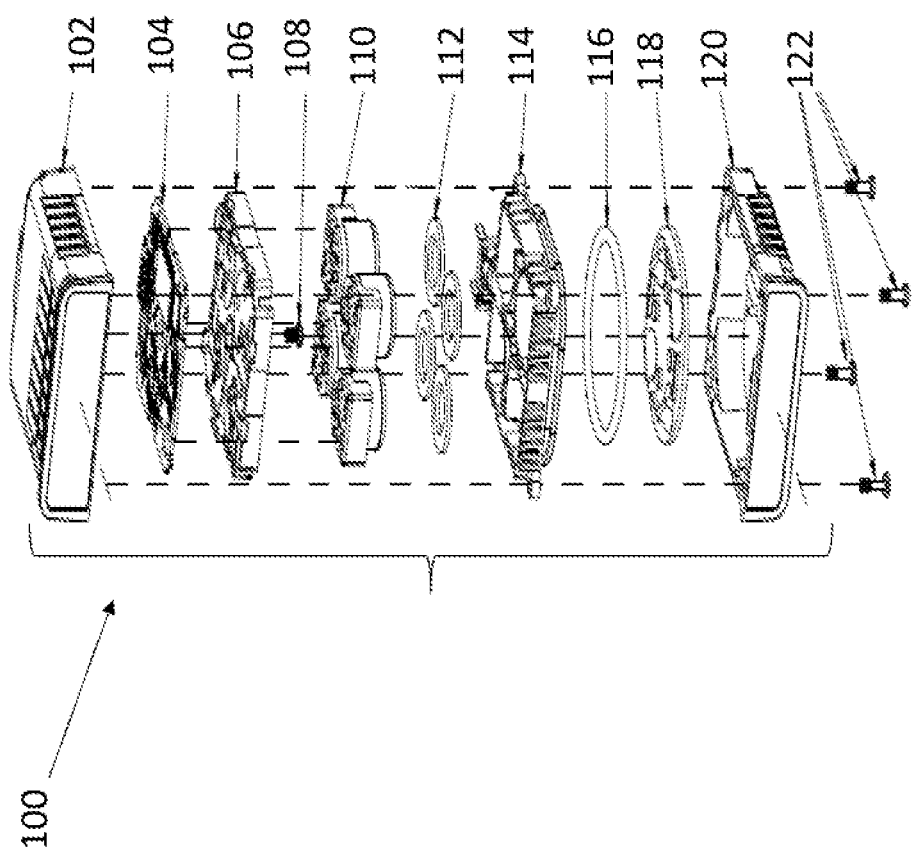
FIG. 3 depicts an exploded view of sensor assembly of a multi-sensor gas detector, in accordance with some example embodiments described herein.

FIG. 3 depicts an exploded view of a sensor assembly of a multi-sensor gas detector 100, in accordance with some example embodiments described herein. Further, the first view of the multi-sensor gas detector 100 illustrated herein at FIG. 3 represents an external structure of the multi-sensor gas detector 100, and the second view at FIG. 3 illustrates an exploded view of the multi-sensor gas detector 100. In accordance with one exemplary embodiment described herein, the exploded view of the multi-sensor gas detector 100 depicts various components and positioning of the various components of the multi-sensor gas detector 100. Starting from a top end of the multi-sensor gas detector 100, FIG. 3 illustrates a housing top cover 102. The housing top cover 102 can comprise a top surface and a bottom surface. Further below the housing top cover 102, a sensor cartridge PCB 104 is positioned. In this regard, in some example embodiments, the sensor cartridge PCB 104 can be mounted on the bottom surface of the housing top cover 102. As illustrated herein, the multi-sensor gas detector 100 further includes a cartridge middle housing 106. In some examples, the cartridge middle housing 106 can be positioned below the sensor cartridge PCB 104 so that a top surface of the cartridge middle housing 106 interfaces with a bottom end of the sensor cartridge PCB 104. In some examples, the bottom surface of the cartridge middle housing 106 can be fixedly attached with the sensor cartridge PCB 104 by using at least one screw 108. Further, in one exemplary embodiment, the cartridge middle housing 106 and the sensor cartridge PCB 104 can be coupled with each other by any attachments means not limited to screw 108, e.g., using a snap fit arrangement, a nut and bolt assembly, or an adhesive.

Further, in one exemplary embodiment, the multi-sensor gas detector 100 further includes a plurality of sensors 110. In accordance with one exemplary embodiment described herein, the plurality of sensors 110 (e.g. sensing die) includes various gas type sensors 110. In addition, at least one sensor of the plurality of sensors 110 includes a sensor head and a sensor PCB. In this regard, the sensor head can be adapted to be exposed with the gas concentration and the sensor PCB can be adapted to determine the current generated by the sensor head. Furthermore, the multi-sensor gas detector 100 includes at least one sensor gasket 112 and a substrate 114. In this regard, the plurality of sensors 110 can be adapted to be held by the substrate 114, In addition, the at least one sensor gasket 112 can be positioned in between the at least one sensor of the plurality of sensors 110 and the substrate 114 in order to seal the plurality of sensors 110. Further, in one exemplary embodiment, the multi-sensor gas detector 100 includes a ring 116 and a disk 118. In this regard, the ring 116 can be adapted to seal the disk 118 with a housing bottom cover 120. In addition, the disk 118 includes a top surface and a bottom surface. Further, the housing bottom cover 120 includes a top surface and a bottom surface.

In accordance with one exemplary embodiment described herein, the top surface of the disk 118 can be adapted to be coupled with a sensor head of the at least one sensor of the plurality of sensors 110. In addition, the bottom surface of the disk 118 can be adapted to be mounted on the top surface of the housing bottom cover 120. Further, in one exemplary embodiment, the housing bottom cover 120 can be coupled with the substrate 114 by using at least one screw 122. Furthermore, the housing bottom cover 120 can be coupled with the substrate 114 by any attachment means and not limited to the screw 122 only. Further, in one exemplary embodiment, the housing bottom cover 120 can be coupled with the substrate 114 by any attachment means and is not limited to the at least one screw 122, e.g., using a snap fit arrangement, a nut and bolt assembly, or an adhesive. Further details of the substrate 114, the disk 118, and an integrated disk assembly formed from a combination of the substrate 114 and the disk 118 are described with reference to FIGS. 2-4.

Figure 4:
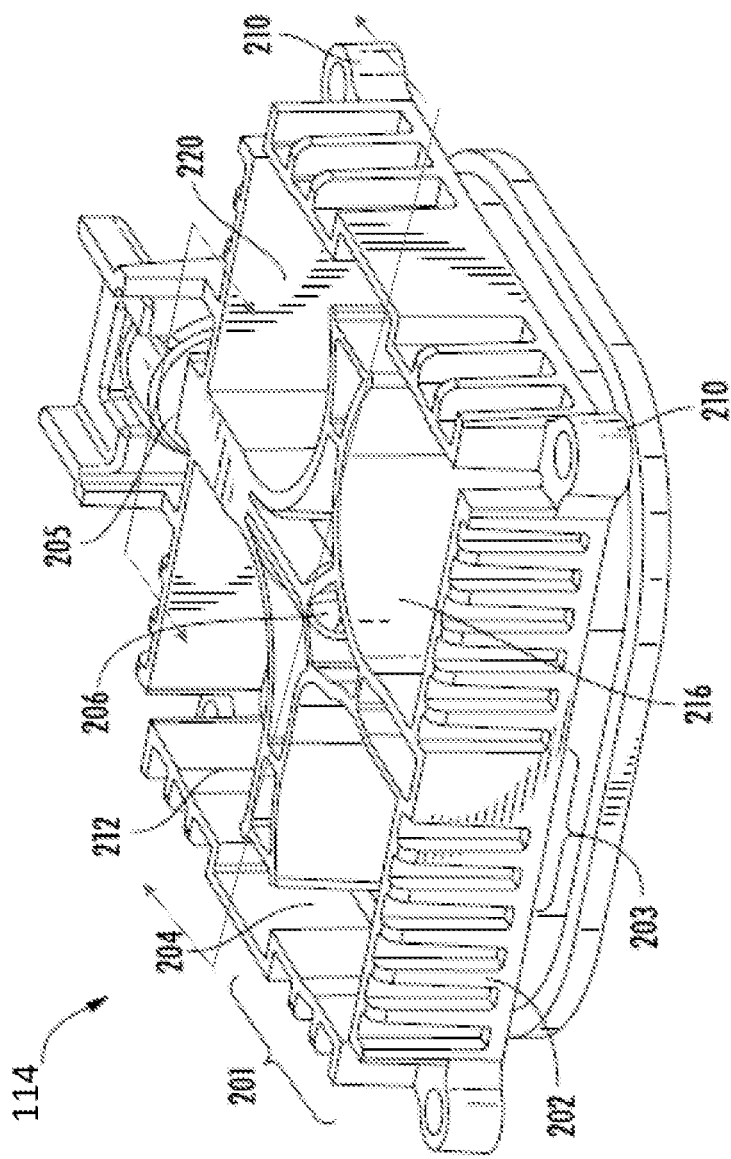
FIG. 4 illustrates a perspective view of a substrate of a multi-sensor gas detector, in accordance with some example embodiments described herein.

FIG. 4 illustrates a perspective view of a substrate 114 of the multi-sensor gas detector 100, in accordance with some example embodiments described herein. In accordance with one exemplary embodiment described herein, the substrate 114 can include a top portion 201 and a bottom portion 203. Top portion 201 includes a number of fins 202. Further, as illustrated, the substrate 114 comprises an outer end 205 of an inlet conduit 206 which can be adapted to allow the ingress of the gas concentration. In this regard, the substrate 114 defines a plurality of openings 204, 212, 216, 220 which are adapted to receive at least one sensor of the plurality of sensors 110 respectively. In accordance with one exemplary embodiment described herein, the substrate 114 can be attached to the housing bottom cover 120 via at least one groove 210. Further, in one exemplary embodiment, the at least one groove 210 can be defined at an outer periphery of the substrate 114. Further, the at least one groove 210 can be adapted to receive the at least one screw 122 to attach the substrate 114 with the housing top cover 102 and the housing bottom cover 120.

Figure 5B:
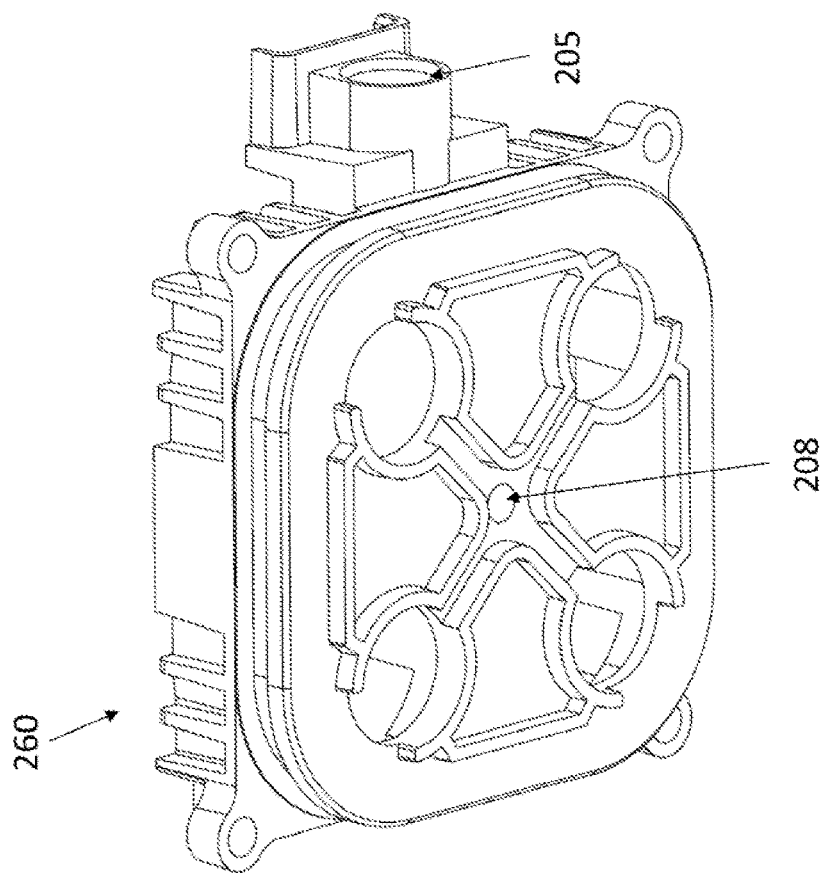
FIG. 5B depicts a bottom view of a substrate, in accordance with some example embodiments described herein.
Figure 5A:
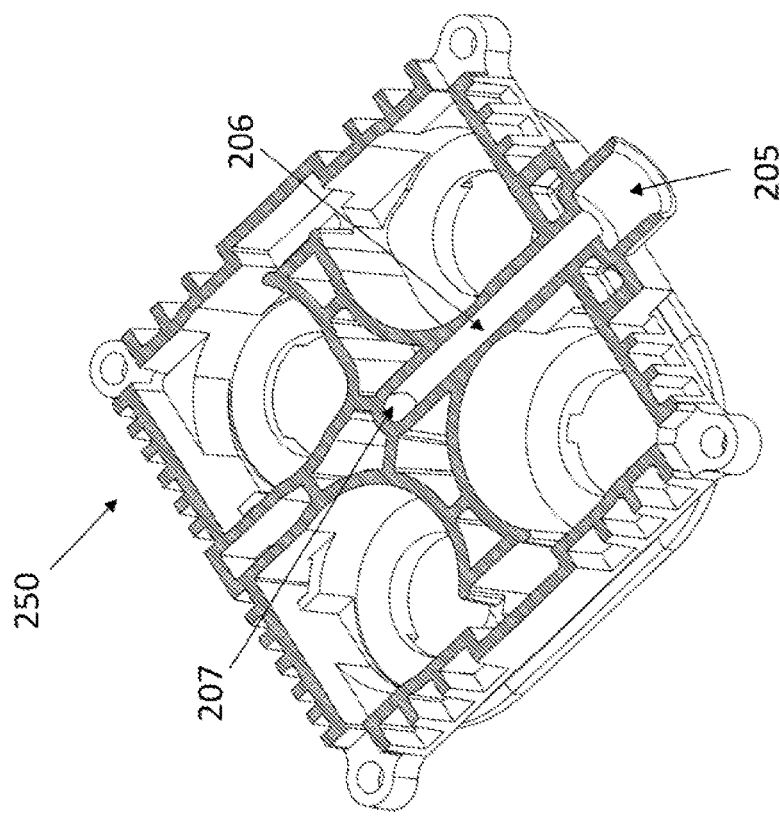
FIG. 5A depicts a bottom sectional view of a substrate through the midpoint of outer end 205, in accordance with some example embodiments described herein.

FIG. 5A and FIG. 5B depict a top view 250 and a bottom view 260 of a substrate (e.g., substrate 114), in accordance with some example embodiments described herein. In one exemplary embodiment, the top view 250 of the substrate indicates the outer end 205, the inlet conduit 206 and a first end 207. In this regard, the bottom view indicates a second end 208 of the inlet conduit 206. Further, in accordance with an embodiment described herein, the inlet conduit 206 can be defined between the first end 207 of the substrate 114 and the second end 208 of the substrate 114. In accordance with one exemplary embodiment described herein, the first end 207 of the inlet conduit 206 can be adapted to receive an inflow of the gas concentration via the outer end 205. Furthermore, in one exemplary embodiment, the second end 208 of the inlet conduit 206 can be exposed to the top surface of the disk 118. In this regard, the disk 118 can be positioned below the substrate 114. To this end, generally, the substrate 114 and the disk 118 define a passage therebetween for the gas concentration to flow from the second end 208 to the sensor head of the at least one sensor of the plurality of sensors 110.

Figure 6:
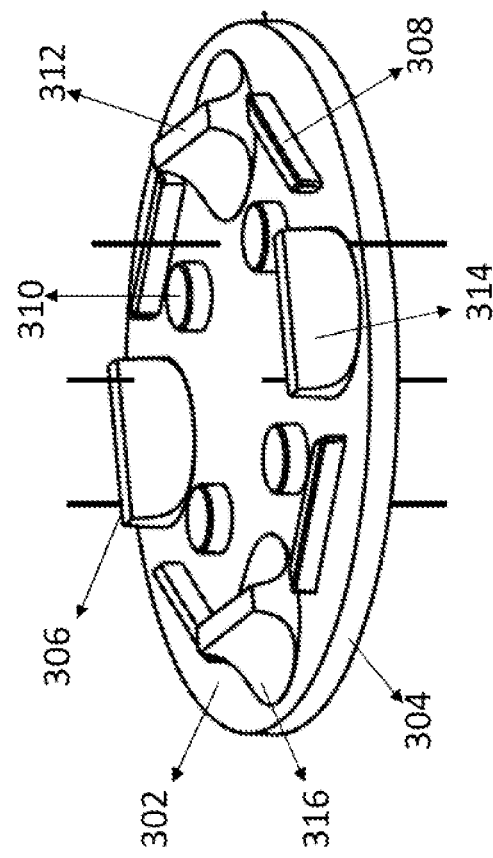
FIG. 6 illustrates a perspective view of a disk of a multi-sensor gas detector, in accordance with some example embodiments described herein.

FIG. 6 illustrates a perspective view of a disk (e.g., disk 118) of the multi-sensor gas detector, in accordance with some example embodiments described herein. As illustrated, the disk 118 includes a top surface 302 and a bottom surface 304. The top surface 302 of the disk 118 includes a plurality of bumps 306, 312, 314, 316 and at least one deflector 308. In addition, the bottom surface 304 of the disk 118 includes at least one groove 310. In accordance with one exemplary embodiment described herein, the substrate 114 (i.e., including the sensing die of the plurality of sensors 110 positioned in respective openings) can be positioned over the disk 118 so that at least one bump 306 can be positioned in proximity with the sensor head of the at least one sensor of the plurality of sensors 110. Further, positioning of the substrate 114 over the disk 118 defines a passage for the gas concentration to pass therethrough from an inlet conduit to an outlet conduit via the first end 207, the second end 208 and a gap 228 defined between the at least one bump 306 and the sensor head. Further details of the passage for gas concentration defined by the bottom portion 203 of the substrate 114 and the top surface 302 of the disk 118 are described in reference to FIGS. 7-12.

In some example embodiments, the disk 118 comprises the at least one groove 310 that can be adapted to receive at least one flange extending from the housing bottom cover 120. In this regard, the disk 118 can be locked with respect to the housing bottom cover 120 based on an engagement of the at least flange into the at least one groove 310. Further, in one exemplary embodiment, the at least one deflector 308 can be adapted to direct the gas concentration towards the sensor head of the at least one sensor of the plurality of sensors 110. In accordance with one exemplary embodiment described herein, the disk 118 can be sandwiched between the housing bottom cover 120 and the substrate 114 in order to provide a uniform flow line to the gas concentration from the second end 208 of the substrate 114 to the sensor head. In one exemplary embodiment, the uniform flow line provides equal gas flow with equal pressure and velocity to the plurality of sensors 110. Further, in one exemplary embodiment, a passage is defined between the substrate 114 and the top surface 302 of the disk 118. In addition, the passage can be equidistant from the plurality of sensors 110. Accordingly, the plurality of sensors 110 can be exposed with the parallel gas flow based on the passage defined by the disk 118.

Figure 7:
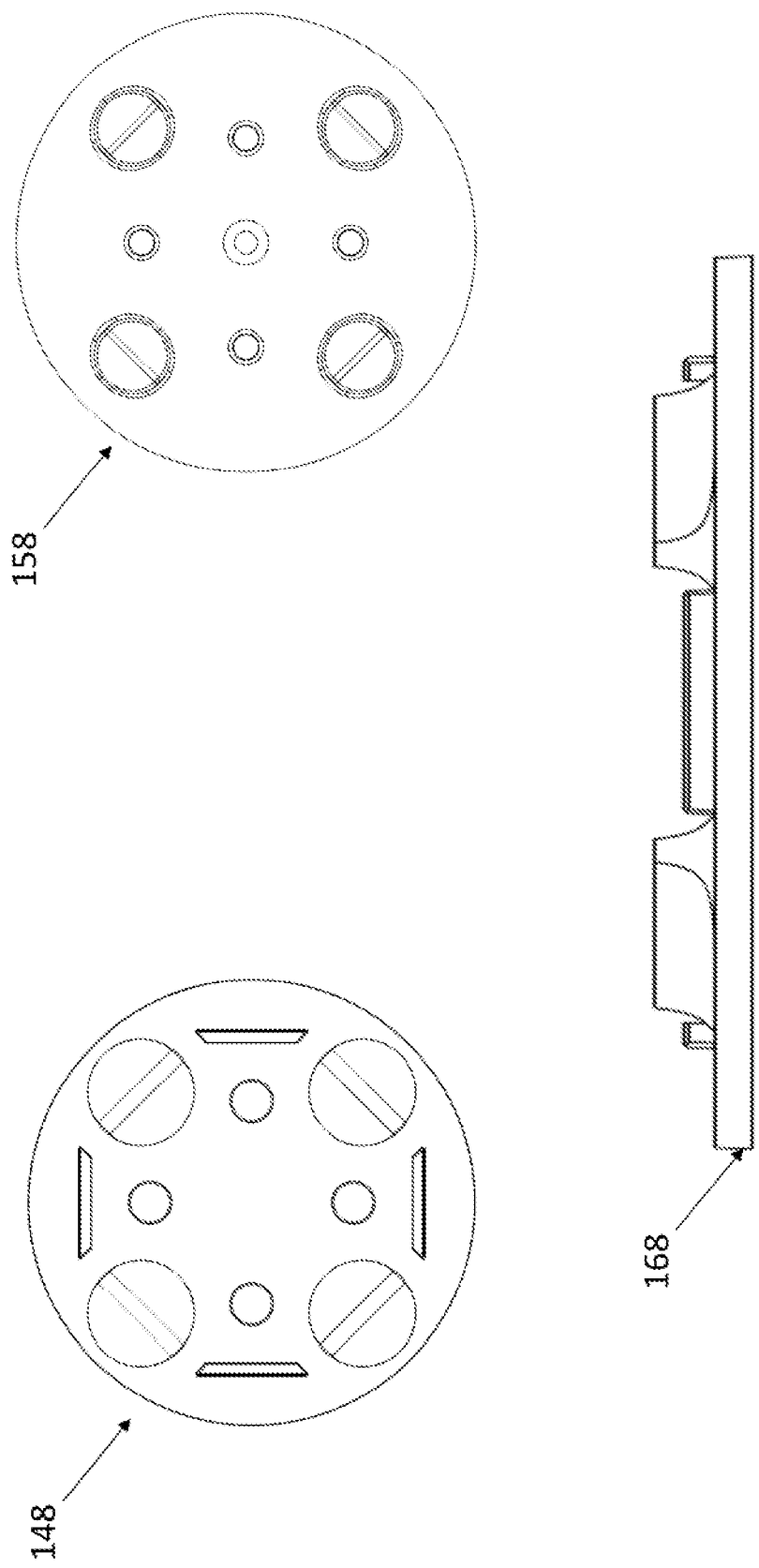
FIG. 7 depicts a top view, a bottom view, and a side view of a disk, in accordance with some example embodiments described herein.

FIG. 7 depicts a top view, a bottom view, and a side view of the disk, in accordance with some example embodiments described herein. In one exemplary embodiment, as shown in FIG. 6, a top view 148 of the disk includes the plurality of bumps (306, 312, 314, and 316) and the at least one deflector 308. Further, in one exemplary embodiment, a bottom view of the disk 158 includes at least one groove 310. In this regard, a side view 168 of the disk 118 includes the plurality of bumps and at least one deflector.

Figure 8:
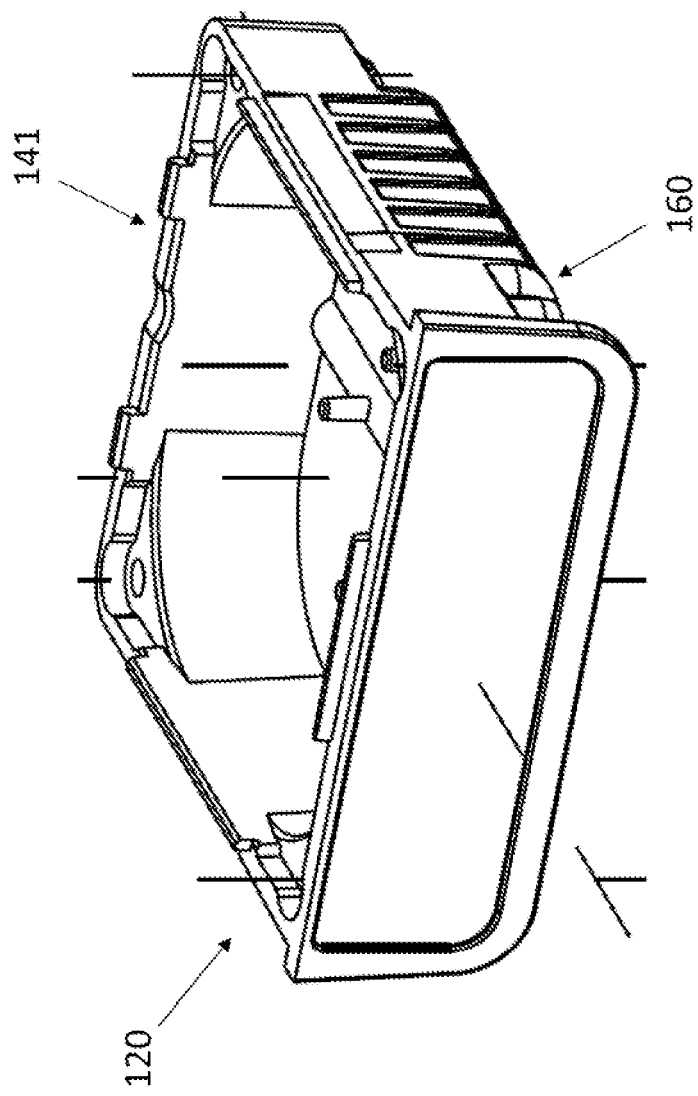
FIG. 8 depicts a perspective front view of a bottom cover of a multi-sensor gas detector, in accordance with some example embodiments described herein.

FIG. 8 depicts a perspective front view of a bottom cover 120 of the multi-sensor gas detector, in accordance with some example embodiments described herein. In one exemplary embodiment, the housing bottom cover 120 includes a top surface 141 surface 141 and a bottom surface 160. Further, in one exemplary embodiment, the housing bottom cover 120 can be adapted to be coupled with the disk 118. In this regard, the detailed description of the top surface 141 of the housing bottom cover 120 can be illustrated with respect to the details provided in FIG. 9.

Figure 9:
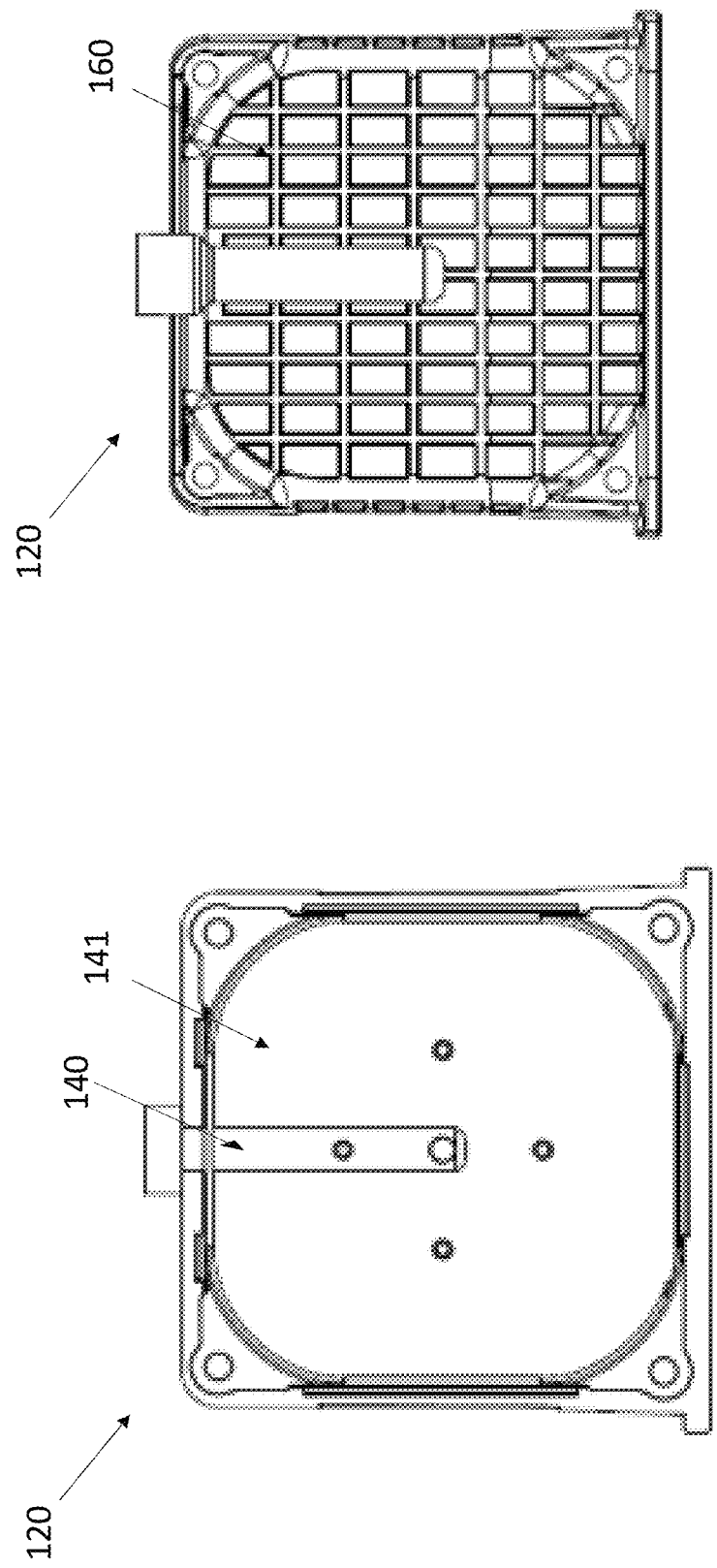
FIG. 9 depicts a top view and a bottom view of a bottom cover, in accordance with some example embodiments described herein.

FIG. 9 depicts a top view and a bottom view of the housing bottom cover 120, in accordance with some example embodiments described herein. In one exemplary embodiment, a top surface 141 of the housing bottom cover 120 illustrates a plurality of elongated members and an outlet conduit. Further, in one exemplary embodiment, the plurality of elongated members can be adapted to fit within the grooves of the disk 118. Further, in one exemplary embodiment, the bottom surface 160 of the housing bottom cover 120 includes a bottom surface and the outlet conduit.

Figure 10:
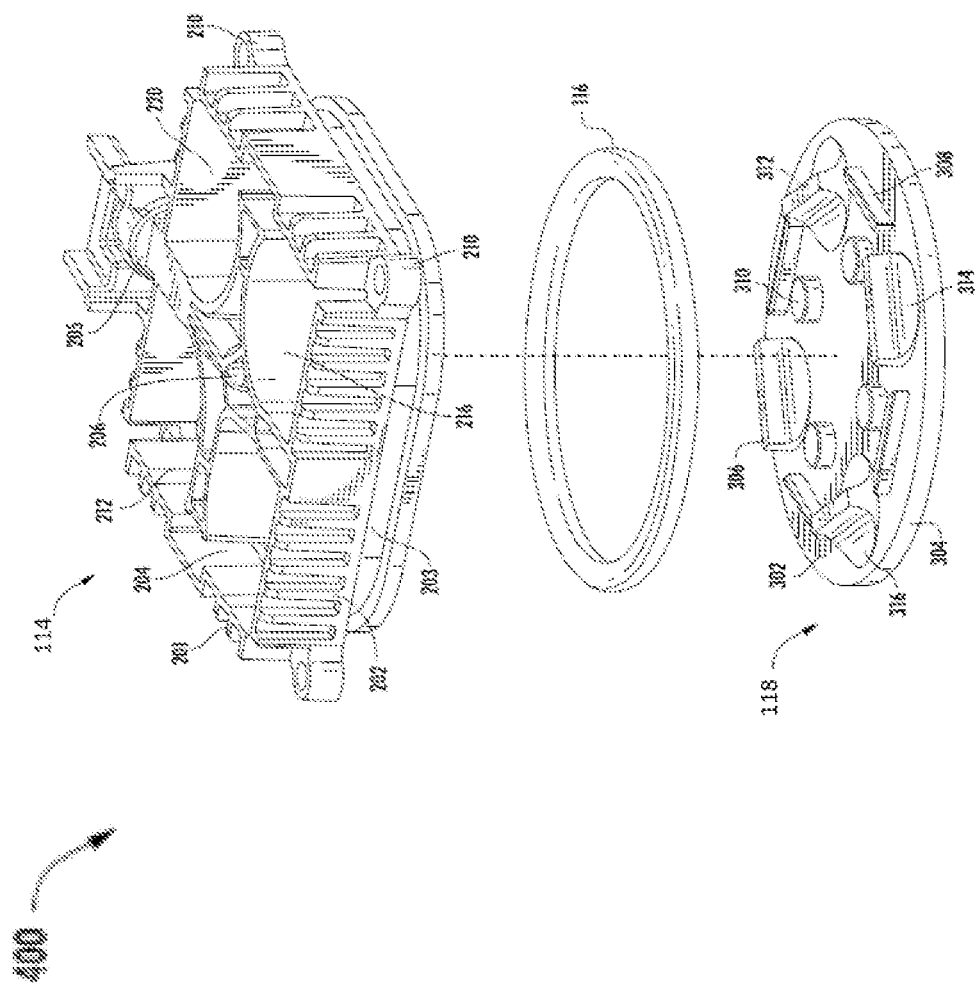
FIG. 10 schematically depicts perspective view of a portion of a sensor assembly of a multi-sensor gas detector, in accordance with some example embodiments described herein.

FIG. 10 schematically depicts a perspective view of a portion of a disk assembly 400 including a sensor assembly of the multi-sensor gas detector, in accordance with some example embodiments described herein. The disk assembly 400 includes the components already described in FIGS. 1-9. Further, in one exemplary embodiment, the disk assembly 400 comprises a multi-sensor assembly as a single housing unit. In accordance with one exemplary embodiment described herein, the disk assembly 400 includes a top surface and a bottom surface. Further, the top surface of the disk assembly 400 includes the substrate 114 and the bottom surface of the disk assembly 400 includes the disk 118. In this regard, the top surface 302 of the disk 118 is positioned in proximity to the substrate 114. Furthermore, the relative positioning of the disk 118 with respect to the substrate 114 provides a passage for the gas concentration to pass therethrough. The passage can be defined between the at least one bump 306 of the disk 118 and the at least one sensor of the plurality of sensors 110. The at least one sensor of the plurality of sensors 110 can be positioned in at least one opening 204 of the substrate 114. Further, in one exemplary embodiment, the ring 116 can be used to seal an interface of the disk 118 and the substrate 114.

Figure 11:
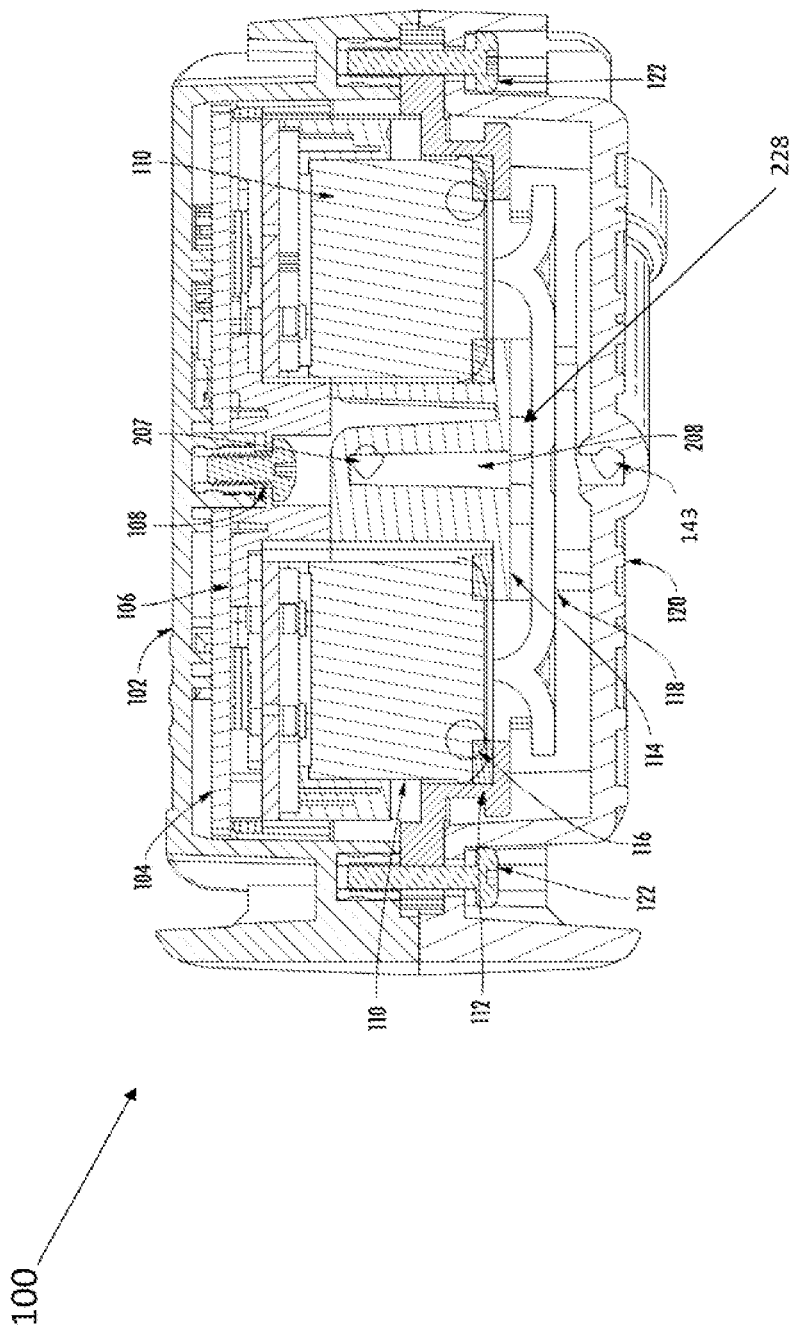
FIG. 11 schematically depicts a sectional view of a multi-sensor gas detector, in accordance with an embodiment described herein.

FIG. 11 schematically depicts a sectional view of the multi-sensor gas detector and an operation performed by the multi-sensor gas detector, in accordance with an embodiment described herein. In accordance with one exemplary embodiment described herein, the structural arrangement of the multi-sensor gas detector 100 shown in FIG. 11 is similar to the multi-sensor gas detector 100, as shown in FIGS. 1-10. In addition, the multi-sensor gas detector 100 as shown in FIG. 11 includes the housing bottom cover 120 which includes the outlet conduit 143. In accordance with one exemplary embodiment described herein, the outlet conduit 140 can include a first end and a second end. In addition, the second end 208 of the inlet conduit 206 can be seen in FIG. 11. As described herein, the inlet conduit 206 has a first end 207 and second end 208.

In accordance with one exemplary embodiment described herein, the substrate 114 can be adapted to hold the plurality of sensors 110 in at least one opening of the substrate 114. In this regard, the at least one sensor of the plurality of sensors 110 is positioned inside at least one opening 204 of the substrate 114 in such a manner that the sensor head of the at least one sensor of the plurality 110 faces towards the at least one bump 306 of the disk 118. In accordance with one exemplary embodiment described herein, the substrate 114 and the disk 118 are coupled with each other resulting in a gap 228 defined between the at least one bump 306 and the at least one sensor 110. Accordingly, this gap 228 or a passage defined by the at least one bump 306 and the at least one sensor head provides uniform gas flow.

In accordance with one exemplary embodiment described herein, the disk 118 is positioned on the bottom portion 203 of the substrate 114 so that the top surface 302 of the disk 118 is exposed to the second end 208 of the inlet conduit 206. Further, in one exemplary embodiment, the disk 118 can be positioned in proximity to the sensor head of the at least one sensor of the plurality of sensors 110. As illustrated in FIG. 11, the at least one bump 306 and the sensor head of the at least one sensor of the plurality of sensors 110 define a passage for the gas concentration to diffuse therethrough. The gas concentration can pass through the first end 207 of the inlet conduit 206 and then pass through the second end 208. The second end 208 can be adapted to direct the gas concentration to pass through the passage and reach at the first end of the outlet conduit 140.

In accordance with one exemplary embodiment described herein, the gas concentration can include a plurality of gases. Further, in one exemplary embodiment, the plurality of sensors 110 can be adapted to detect the plurality of gases present in the gas concentration. In addition, the multi-sensor gas detector 100 can be adapted to determine the gas concentration and flow rate of the plurality of gases.

Further, in one exemplary embodiment, the inlet conduit 206 can be defined along a first axis of the substrate 114. As illustrated herein, the outlet conduit can be defined along a second axis of the housing bottom cover 120. Further, in one exemplary embodiment, the first axis and the second axis can be orthogonal to each other.

In accordance with one exemplary embodiment described herein, the first end of the outlet conduit 140 can be mounted at a central axis of the housing bottom cover 120 and the second end of the outlet conduit 140 can be mounted on an outer periphery of the housing bottom cover 120.

In one exemplary embodiment of the invention, the plurality of sensors 110 can be in fluidic communication with the disk 118 of the multi-sensor gas detector 100. The disk 118 may be operable to facilitate a uniform inflow of the gas concentration inside the multi-sensor gas detector 100. The gas concentration provided by the first end 207 of the inlet conduit 206 may extend through the passage defined between the bottom surface of the substrate 114 and the top surface of the disk 118. During operation of the multi-sensor gas detector 100, the target gas may be communicated into or caused to diffuse within the multi-sensor gas detector 100 for the purposes of gas concentration measurement and/or monitoring.

According to various exemplary embodiments, the multi-sensor gas detector 100, or components thereof, may be operable to monitor a concentration of the target gas, for example oxygen or carbon monoxide, based on a diffusion of the target gas inside the multi-sensor gas detector 100. To this extent, the sensor head of the at least one sensor of the plurality of sensors 110 may consume the target gas and generate a current signal, such that measurement of the concentration of the target gas can be achieved by measuring the current signal. Further, in one exemplary embodiment, the current may be generated due to the electrochemical reaction inside the multi-sensor gas detector 100.

In some embodiments, the multi-sensor gas detector 100 can optionally include the sensor cartridge PCB 104 comprising a processing circuitry that may be configured to receive a digitized output indicative of values corresponding to the electric current or the voltage generated inside the multi-sensor gas detector 100. In this aspect, in accordance with various example embodiments described herein, the processing circuitry may process such values to determine a concentration of the target gas. In another example embodiment, sensor cartridge PCB 104 and the processing circuitry may be located external to the multi-sensor gas detector 100.

In one of the exemplary embodiments, a sensor assembly includes a substrate and a disk for providing parallel gas flow to the plurality of sensing dies. Further, the substrate defines a plurality of openings adapted to receive at least one sensing die of a plurality of sensing dies. In addition, the substrate defines an inlet conduit between a first end and a second end. The first end of the substrate is adapted to receive an inflow of a gas concentration. In accordance with one exemplary embodiment described herein, the disk includes a top portion and a bottom portion. Further, the disk is adapted to be positioned below the substrate so that the top portion of the disk is exposed to the second end 208 of the inlet conduit 206 and the disk 118 defines a passage for the gas concentration to flow from the second end 208 to a sensor head of the at least one sensing die.

Further, in another exemplary embodiment, the sensor assembly includes a housing having a top portion and a bottom portion. Further, in one exemplary embodiment, the top portion includes a substrate that defines a plurality of openings. In addition, the bottom portion of the housing includes a disk including a top portion and a bottom portion. In accordance with one exemplary embodiment described herein, the plurality of openings is adapted to receive at least one sensing die of a plurality of sensing dies. In addition, the substrate further defines an inlet conduit between a first end of the substrate and a second end of the substrate. In this regard, the first end is adapted to receive an inflow of a gas concentration. Further, the disk is adapted to be positioned below the substrate so that the top portion of the disk is exposed to the second end of the inlet conduit and the disk defines a passage for the gas concentration to flow from the second end to a sensor head of the at least one sensing die.

Further, in another exemplary embodiment, the sensor assembly is configured for providing parallel gas flow to a plurality of sensors. In accordance with one exemplary embodiment described herein, the sensor assembly includes a housing, which includes a top cover and a bottom cover, and a substrate positioned between the top cover and the bottom cover. Further, the substrate defines a plurality of openings and an inlet conduit. In this regard, the plurality of openings is adapted to receive at least one sensor of a plurality of sensors. In addition, the inlet conduit is defined between a first end of the substrate and a second end of the substrate. In accordance with one exemplary embodiment described herein, a disk includes a top portion and a bottom portion such that the top portion of the disk and a portion of the substrate defines a passage for a gas concentration to flow from the second end to a sensor head of the at least one sensor.

In accordance with one exemplary embodiment described herein, the top cover of the housing includes an inner portion and an outer portion. In addition, the bottom cover of the housing includes an inner portion and an outer portion. In this regard, the inner portion of the top cover and the inner portion of the bottom cover are adapted to cover and protect the substrate and other internal components.

In accordance with one exemplary embodiment described herein, the inlet conduit is configured to provide a parallel gas flow via the plurality of flow lines. Further, in another embodiment of the invention, the second end of the inlet conduit is equidistant from the plurality of sensors.

In accordance with one exemplary embodiment described herein, the inner portion of the housing bottom cover includes a plurality of locking elements. Further, in one exemplary embodiment, the plurality of locking elements is adapted to be locked with the plurality of grooves.

In accordance with one exemplary embodiment described herein, the sensor assembly further includes an outlet conduit mounted on the inner portion of the bottom cover. Further, in one exemplary embodiment, the outlet conduit includes a first opening at a central axis of the inner portion of the bottom cover and a second opening at an outer periphery of the outer portion of the bottom cover.

In accordance with one exemplary embodiment described herein, the second end of the inlet conduit comprises a plurality of flow lines extending from the second end to the first end of the outlet conduit via the passage.

In accordance with one exemplary embodiment described herein, the first end is configured to provide ingress of the gas concentration therethrough and the second end is configured to provide an egress of the gas concentration via the passage.

In accordance with one exemplary embodiment described herein, the top portion of the disk defines a plurality of bumps and a plurality of ribs. Further, in one exemplary embodiment, at least one bump of the plurality of bumps is in proximity to the sensor head and defines a channel between the at least one bump and the sensor head.

In accordance with one exemplary embodiment described herein, the bottom portion comprising an inner surface and an outer surface. Further, in one exemplary embodiment, the bottom surface of the disk is mounted on the inner surface of the bottom cover.

In accordance with one exemplary embodiment described herein, the inlet conduit can be at a first central axis of the substrate. In addition, the outlet conduit is at a first central axis of the bottom cover. In this regard, the first central axis of the inlet conduit is orthogonal to the first central axis of the outlet conduit. Further, the inlet conduit and the outlet conduit are equidistant from the plurality of sensors.

According to some example embodiments described herein, the disk assembly can be adapted to determine rate of flow of the target gas and concentration of the target gas. In addition, the plurality of sensors includes at least four sensors which are adapted to detect a first gas.

According to some example embodiments described herein, the plurality of sensors includes at least four sensors which are adapted to detect a plurality of gases.

In some example embodiments, certain operations described herein may be modified or further amplified as described below. Moreover, in some embodiments additional optional operations may also be included. It should be appreciated that each of the modifications, optional additions or amplifications described herein may be included with the operations herein either alone or in combination with any others among the features described herein.

The foregoing method descriptions and the process flow diagrams are provided merely as illustrative examples and are not intended to require or imply that the steps of the various embodiments must be performed in the order presented. As will be appreciated by one of skill in the art, the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

Many modifications and other embodiments of the inventions set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the supply management system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

The invention claimed is:

1. A sensor assembly, comprising:
a housing having a top cover and a bottom cover;
a substrate positioned between the top cover and the bottom cover, the substrate defining:
a plurality of openings, each opening adapted to receive one sensor having a sensor head of a plurality of sensors having respective sensor heads; and
an inlet conduit between a first end of the substrate and a second end of the substrate, the first end adapted to receive an inflow of a gas; and
a disk comprising a top portion and a bottom portion, the disk positioned below the substrate so that the top portion of the disk is exposed to the second end of the substrate and, wherein the disk defines a passage for the gas to flow from the first end of the substrate to the sensor head of the one sensor, wherein the passage is adapted to circulate the gas to the plurality of openings with uniform pressure and flow-rate of the gas, and wherein the passage is defined such that the second end of the substrate is equidistant from the respective sensor heads of the plurality of sensors.

2. The sensor assembly of claim 1, wherein the top cover comprises an inner portion and an outer portion and the bottom cover comprises an inner portion and an outer portion, and wherein the inner portion of the top cover and the inner portion of the bottom cover are configured to enclose the substrate.

3. The sensor assembly of claim 2, wherein the bottom portion of the disk is mounted on the inner portion of the bottom cover.

4. The sensor assembly of claim 2, wherein the bottom portion of the disk defines a plurality of grooves.

5. The sensor assembly of claim 4, wherein the inner portion of the bottom cover includes a plurality of locking elements, and wherein the plurality of locking elements is adapted to be locked with the plurality of grooves.

6. The sensor assembly of claim 2, further comprising an outlet conduit mounted on the inner portion of the bottom cover, wherein the outlet conduit includes a first opening at a central axis of the inner portion of the bottom cover and a second opening at an outer periphery of the outer portion of the bottom cover.

7. The sensor assembly of claim 6, wherein the inlet conduit comprises a plurality of flow lines extending from the second end to the first end via the passage.

8. The sensor assembly of claim 1, wherein the first end is configured to provide ingress of the gas therethrough and the second end is configured to provide an egress of the gas via the passage.

9. The sensor assembly of claim 1, wherein the top portion of the disk includes at least one bump, and wherein the substrate and the disk are coupled such that a gap is defined between the at least one bump and the at least one sensor to allow the gas to flow from the first end of the substrate to the sensor head of the at least one sensor via the second end and the gap.

10. A disk assembly, comprising:
a housing having a top cover and a bottom cover;
a substrate positioned between the top cover and the bottom cover of the housing, wherein the substrate defines:
a plurality of openings, each opening adapted to receive one sensor having a sensor head of a plurality of sensors having respective sensor heads; and
an inlet conduit between a first end of the substrate and a second end of the substrate, wherein the first end is adapted to receive an inflow of a gas,
wherein the bottom cover of the housing includes a disk, wherein the disk comprises a top portion and a bottom portion, wherein the disk is adapted to be positioned immediately adjacent the substrate so that the top portion of the disk is exposed to the second end of the substrate, wherein the disk defines a passage for the gas to flow from the first end of the substrate to the sensor head of the one sensor, wherein the passage is adapted to circulate the gas to the plurality of openings with uniform pressure and flow-rate of the gas, and wherein the passage is defined such that the second end of the substrate is equidistant from the respective sensor heads of the plurality of sensors.

11. The disk assembly of claim 10, wherein the bottom cover of the disk comprises an inner surface and an outer surface, wherein a bottom surface of the disk is mounted on the inner surface of the bottom cover.

12. The disk assembly of claim 11, further comprising an outlet conduit mounted on the inner surface of the bottom cover, wherein the outlet conduit includes a first opening at a central axis of the inner portion and a second opening at an outer periphery.

13. The disk assembly of claim 10, wherein the first end of the substrate is configured to provide ingress of the gas therethrough and the second end of the substrate is configured to provide an egress of the gas via the passage.

14. A sensor assembly for providing parallel gas flow to a plurality of sensors, comprising:
a housing having a top cover and a bottom cover;

a substrate positioned between the top cover and the bottom cover, the substrate defining:

a plurality of openings, each opening adapted to receive one sensor having a sensor head of the plurality of sensors having respective sensor heads, and an inlet conduit comprising a first end and a second end, wherein the first end is adapted to receive an inflow of a gas; and a disk comprising a top portion and a bottom portion, the disk being positioned below the substrate such that the top portion of the disk is exposed to the second end of the substrate, wherein the top portion of the disk and a portion of the substrate defines a passage for a gas to flow from the second end of the inlet conduit to the sensor head of the one sensor, wherein the disk defines a passage for the gas to flow from the first end of the inlet conduit of the sensor head of the one sensor, wherein the passage is adapted to circulate the gas to the plurality of openings with uniform pressure and flow-rate of the gas, and the passage is defined such that the second end of the inlet conduit is at equal distance from each of the respective sensors of the plurality of sensors.

15. The sensor assembly of claim 14, wherein the top cover and the bottom cover are configured to enclose the substrate.

16. The sensor assembly of claim 15, wherein the bottom cover comprises an inner surface and an outer surface, and wherein a bottom surface of the disk is mounted on the inner surface of the bottom cover.

17. The sensor assembly of claim 16, further comprising an outlet conduit mounted on the inner surface of the bottom cover, wherein the outlet conduit includes a first opening at a center of the inner surface and a second opening at an outer periphery of the outer surface.

18. The sensor assembly of claim 17, wherein the second end of the inlet conduit comprises a plurality of flow lines extending from a second end to a first end of the outlet conduit via the passage.

19. The sensor assembly of claim 14, wherein the first end of the inlet conduit is configured to provide ingress of the gas therethrough and the second end of the inlet conduit is configured to provide an egress of the gas via the passage.

* * * * *